| United States Patent [19] | [11] Patent Number: 4,753,801 |
| Oren et al. | [45] Date of Patent: Jun. 28, 1988 |

[54] SUSTAINED RELEASE TABLETS

[75] Inventors: Peter L. Oren, Noblesville; Werner M. K. Seidler, Indianapolis, both of Ind.

[73] Assignee: Eli Lilly and Company, Indianapolis, Ind.

[21] Appl. No.: 791,282

[22] Filed: Oct. 25, 1985

[51] Int. Cl.⁴ .......................... A61K 9/22; A61K 9/26
[52] U.S. Cl. ...................................... 424/465; 424/80; 424/469
[58] Field of Search .............................. 424/468–470, 424/80, 465

[56] References Cited

U.S. PATENT DOCUMENTS 4,264,573  4/1981  Powell et al. .......................... 424/19
4,465,660  8/1984  David et al. ........................... 424/15

OTHER PUBLICATIONS

Chowhan et al., *Journal of Pharmaceutical Sciences*, vol. 67, No. 10, 1385–1389 (1978).

Primary Examiner—Michael R. Lusignan
Attorney, Agent, or Firm—Bruce J. Barclay; Leroy Whitaker

[57] ABSTRACT

The present invention provides sustained release tablets in unit dosage form comprising an active agent which has low aqueous solubility.

4 Claims, No Drawings

SUSTAINED RELEASE TABLETScl

BACKGROUND OF THE INVENTION

A variety of methods are known to formulate pharmaceutical compositions to provide various release patterns of the active agent from the composition. However, research continues in an effort to develop improved compositions capable of delivering pharmaceutical agents in a sustained and predictable manner.

Compositions containing active agents which exhibit low aqueous solubility are difficult to formulate in such a manner so as to promote the uniform, sustained release of the agent from the composition. The present compositions provide excellent dissolution of an active agent having low aqueous solubility from a tablet composition wherein a large percentage of the composition is the active agent itself.

SUMMARY OF THE INVENTION

The present invention relates to a sustained release pharmaceutical formulation in tablet unit dosage form which provides prolonged plasma levels of an active agent and comprises about 60.0% to about 80.0% by weight of the active agent, about 1.0% to about 15.0% by weight of a pharmaceutically acceptable excipient, about 3.0% to about 15.0% by weight of a disintegrant, about 2.0% to about 10.0% by weight of a pharmaceutically acceptable binder and about 0.5% to about 3.0% by weight of a tablet lubricant.

DETAILED DESCRIPTION OF THE INVENTION

Amounts and percentages are described in this document as weight units unless otherwise stated.

The percent of the ingredients required in the formulation of the invention, namely the active agent, the excipient, the disintegrant, the binder and the tablet lubricant, is calculated on a dry weight basis without reference to any water or other components present. Thus, these five components together constitute 100 percent of the formulation for purposes of calculating individual percentages. If additional ingredients are present in the formation, then the actual percentages for these five ingredients will change accordingly but their relative concentrations to each other will remain the same. If other ingredients are present, the sum of all of the components constitutes 100 percent of the formulation for purposes of calculating individual percentages with the exception of the film coating.

The term "unit dosage form", as employed in the specification, refers to physically discrete units suitable as unitary dosages for human subjects and other mammals, each unit containing a predetermined quantity of active material calculated to produce the desired therapeutic effect, in association with the other ingredients of the formulation disclosed herein.

The active agents employed herein exhibit low aqueous solubility. An active agent will be present in the formulations of the invention at a concentration in the range of about 60.0% to about 80.0% by weight, preferably from about 65.0% to about 75.0% by weight. The active agents employed in the present formulations are typically those of the class commonly referred to as non-steroidal anti-inflammatories (NSAIDS). Many of these agents are weakly acidic in nature and hence typically exhibit relatively low aqueous solubility at lower pH values. The preferred active agent of this type is fenoprofen, and especially fenoprofen calcium. However, a variety of agents may be employed in the formulation and include the salicylate derivatives such as aspirin and sodium salicylate; the pyrazolon derivatives such as phenyl butazone, oxyphenbutazone and apazone; indomethacin and sulindac; derivatives of N-phenyl anthranilic acid such as mefenamic, meclofenamic, flufenamic, tolfenamic and etofenamic acids; tolmetin sodium; propionic acid derivatives such as ibuprofen, naproxen, flurbiprofen and ketoprofen; and related compounds. Additional examples of active agents include that class of compounds which are acidic in nature and which possess the solubility characteristics described above.

The formulations of the invention will also contain from about 1.0% to about 15.0% by weight of a pharmaceutically acceptable excipient, more preferably in the range of about 5.0% to about 12.0% by weight. These excipients should be water soluble and chemically inert to the other ingredients. While the preferred excipient is lactose, a variety of other known and commonly used excipients may be used such as mannitol, glucose, fructose, xylose, galactose, sucrose, maltose, xylitol, sorbitol, as well as other pharmaceutically acceptable monosaccharides and disaccharides. Other suitable excipients would include inorganic compounds such as the chloride, sulfate and phosphate salts of potassium, sodium and magnesium, as well as calcium, lactate, gluconate and succinate salts.

The present formulation will also contain a disintegrant at a concentration in the range of about 3.0% to about 15.0% by weight, more preferably from about 5.0% to about 9.0% by weight. While a variety of disintegrants may be used in the formulation, the preferred disintegrant is starch powder. Other suitable disintegrants include the modified starches, for example, sodium carboxymethyl starch; cellulose derivatives such as microcrystalline celluloses (Avicel PH 101), or colloidal microcrystalline cellulose with carboxymethyl cellulose added as a dispersant (Avicel RC-591) and cross linked types (Ac-Di-Sol), water soluble cellulose derivatives such as methyl cellulose, sodium carboxymethyl cellulose, and hydroxypropyl methyl cellulose; aliginic acid, sodium alginate, clays, cross-linked polyvinylpyrrolidone, ion exchange resins or other disintegrants which are well known to those familar with pharmaceutical formulations. These disintegrants may be added to the formulation either in the granulation step, known as intragranular disintegrants, or after the granulation step but before the compression step, which are known as extragranular disintegrants.

The formulations of the invention will also contain a pharmaceutically acceptable binder. This binder will be present at a concentration in the range of about 2.0% to about 10.0% by weight, more preferably from about 2.0% to about 6.0% by weight. The preferred binders are pregelatinized starch and povidone. Other pharmaceutically acceptable binders include sucrose, lactose, gelatin, starch paste, acacia, tragacanth, and other gums; cellulose derivatives such as methyl cellulose, sodium carboxymethyl cellulose, hydroxypropyl methyl cellulose, hydroxypropyl cellulose, and ethyl cellulose; microcrystalline cellulose; polyethylene glycols; corn syrup; or other binders known to those familiar with pharmaceutical formulations.

The present formulations will also contain a tablet lubricant. The lubricant will be present in the formulation at a concentration in the range of about 0.5% to about 3.0% by weight, preferably from about 1.0% to about 2.0% by weight. The preferred lubricants are stearic acid, in powder form, and magnesium stearate. Other suitable tablet lubricants are calcium or zinc stearate, hydrogenated vegetable oils, talc, polyethylene glycols, mineral oil or other pharmaceutically acceptable die wall lubricants.

The present formulations may also contain a surface active agent at a concentration in the range of about 0.1% to about 2.0% by weight, preferably from about 0.2% to about 1.0% by weight, and its presence is preferred. The preferred agent is sodium lauryl sulfate. However, other agents may also be employed such as DSS (dioctyl sodium sulfosuccinate), triethanolamine, polyoxyethylene sorbitan and poloxalkol derivatives, quaternary ammonium salts or other pharmaceutically acceptable surface active agents. Additionally, the lubricants and surface active agents can be combined and incorporated in the formulation as a single ingredient.

An additional disintegrant is preferably added to the present formulation following granulation of the formulation ingredients but prior to forming the tablets. This extragranular disintegrant will be present from about 0.1% to about 15% by weight, more preferably from about 1.0% to about 5.0% by weight. The extragranular disintegrant may be chosen from those described above, with the preferred extragranular disintegrant being cellulose with sodium carboxymethylcellulose.

The present formulation may also contain a hydrophobic retarding agent. This agent will be present at a concentration in the range of about 0.1% to about 15.0% by weight, more preferably from about 2.0% to about 8.0% by weight. Depending on the manufacturing method employed (discussed infra), the inclusion of this ingredient in the formulation may not be required to yield the proper release pattern. Preferably, stearic acid powder is used, but other suitable agents include purified grades of beeswax; fatty acids; long chain fatty alcohols, such as cetyl alcohol, myristyl alcohol, and stearyl alcohol; glycerides such as glyceryl esters of fatty acids like glyceryl monostearate, glyceryl distearate, glyceryl esters of hydrogenated castor oil and the like; oils such as mineral oil and the like, or acetylated glycerides; ethyl cellulose, vegetable oil derivatives, paraffin, carnauba wax, talc; and the stearate salts such as calcium, magnesium, and zinc.

If desired, other conventional tablet ingredients such as preservatives, stabilizers, glidants, and FD&C colors may be included in the formulation. These ingredients may be included at a concentration of about 0.1% to about 2.0% by weight. Acceptable glidants or flow enhancers include such agents as colloidal silicon dioxide and talc. Coloring agents may be incorporated into the formulation by various methods but a particularly preferred procedure is the addition of appropriate dye dispersions such Opaspray, marketed by Colorcon, Inc., West Point, Pennsylvania, to the granulating solution.

The resulting tablets may be coated, if desired, with one of many readily available coating systems. Coating the tablets serves to mask the taste of the drug, make the tablet easier to swallow and, in some cases, improve the appearance of the dosage form. The tablets can be sugar coated according to procedures well known in the art, or can be coated with any one of numerous polymeric film coating agents frequently employed by formulation chemists. Representative examples of such film coating agents include hydroxypropyl methyl cellulose, carboxymethylcellulose, hydroxypropyl cellulose, methyl cellulose, ethyl cellulose, acrylic resins, povidone, polyvinyl diethylaminoacetate, cellulose acetate phthalate, polyvinyl acetate phthalate, hydroxypropyl methyl cellulose phthalate, acrylic latex emulsions, ethyl cellulose latex emulsions or other commercially available preparations such as Pharmacoat, manufactured by Shin-Etsu Chemical Co., Ltd., Ohtemachi, Chiyodaku Tokyo, Japan, and Opadry, manufactured by Colorcon, Inc.

The present formulations may be prepared by procedures well known by formulation chemists. However, it has been determined that the granulator employed in the manufacture of a formulation of the invention plays an important role in the release rate which the final formulation will have. For example, when using a granulator which imparts high energy to the formulation by the rapid turning of the mixing blades, the granules which are formed are typically spherical and more compact, possessing lower porosity than those produced by low energy granulators. As such, formulations prepared with a high energy granulator may require increased amounts of excipient and disintegrant in order to draw greater amounts of water into the formulation in order to promote release of the active agent. The preferred high energy granulator is the Diosna mixer available from Dierks and Sohne Maschinefabrik. In contrast, a low energy granulator may also be employed to prepare the present compositions which typically results in a formulation having a faster rate of release as compared to a formulation prepared with a high energy granulator. As such, formulations prepared with a low energy granulator will typically need less excipient and disintegrant than may be otherwise employed, and may require a hydrophobic retarding agent. While a number of low energy granulators may be employed, the preferred low energy granulators are planetary mixers such as a Pony mixer and especially a Hobart mixer.

A particularly preferred formulation of the invention is as follows:

| Ingredient | Percent by Weight |
| --- | --- |
| fenoprofen calcium | about 67.0% to about 72.0% |
| pharmaceutically acceptable excipient | about 5.0% to about 12.0% |
| disintegrant | about 5.0% to about 9.0% |
| pharmaceutically acceptable binder | about 2.0% to about 6.0% |
| tablet lubricant | about 1.0% to about 2.0% |
| surface active agent | about 0.2% to about 1.0% |

A more highly preferred formulation of the present invention may be represented by the following:

| Ingredient | Percent by Weight |
| --- | --- |
| fenoprofen calcium | about 70.0% |
| lactose | about 10.0% |
| starch powder | about 7.0% |
| cellulose with sodium carboxymethylcellulose | about 3.0% |
| pregelatinized starch | about 3.0% |
| povidone | about 3.0% |
| stearic acid | about 1.0% |
| magnesium stearate | about 0.5% |
| sodium lauryl sulfate | about 0.25% |

The formulations of the invention will have a prolonged in vitro release rate. The in vitro test used to measure release rate of the active agent from a formulation of the invention was as follows. A solution of 1000 ml of a 0.05 M pH 4.5 monobasic potassium phosphate solution was placed in an apparatus capable of agitation. The apparatus contained a paddle and rotated at a speed of 100 rpm. The tablet formulation was placed in the apparatus and dissolution was periodically measured.

The following Examples further illustrate the formulations of the invention, and methods for their preparation. The Examples are not intended to be limiting to the scope of the invention in any respect and should not be so construed.

Example 1 illustrates the preferred formulation when prepared with a high energy granulator such as a Diosna mixer.

EXAMPLE 1

Mixture A was prepared as follows: A Diosna mixer was charged with 17.5 kg of fenoprofen calcium, 2.64 kg of lactose, 1.75 kg of starch powder and 656 g of pregelatinized starch through a No. 10 mesh screen. The mixture was blended for five minutes using a low speed mixer and low speed chopper settings. While continuing to mix as described above, 4373 ml of a 15% w/v aqueous povidone solution was added slowly. The mixture was then agitated using a high speed mixer and high speed chopper settings for three minutes. During this time, purified water was added to the mixture in a quantity sufficient to produce a satisfactory granulation. The granulation was then wet sieved through a No. 6 screen onto paper-lined trays. The granulation was dried at 110° F. for 16 hours. The dried granulation was milled at 1400 rpm with a Fitz mill into a clean, polyethylene lined drum yielding 22.32 kg of mixture A. The mill employed a 2AA plate with knives forward.

A second mixture, hereinafter termed "mixture B", was prepared as follows. To a Diosna mixer was added 26.25 kg of fenoprofen calcium, 3.965 kg of lactose, 2.625 kg of starch powder and 984.5 g of pregelatinized starch. The mixture was blended for five minutes using a low speed mixer and low speed chopper settings. While continuing to mix as described above, 6563 ml of a 15% w/v aqueous povidone solution containing 495 g of Opaspray Butterscotch L-2701 (Manufactured by Colorcon, Inc.) was added slowly. The mixture was then agitated using a high speed mixer and high speed chopper settings for three minutes. During this time, purified water was added in a quantity sufficient to produce a satisfactory granulation. The wet granulation was sieved using a No. 6 screen onto paper-lined trays. The granulation was dried at 110° F. for 16 hours.

A third mixture, mixture C, was prepared in the same manner as mixture B. After drying, this mixture was combined with mixture B and milled at 1400 rpm with a Fitz mill into a clean polyethylene lined drum yielding 68.03 kg of mixture BC. The mill employed a 2AA plate with knives forward.

A ribbon mixer was charged with 11.6 kg of mixture A and 35.3 kg of mixture BC. To this mixture was added 1.5 kg of cellulose with sodium carboxymethylcellulose-591 (Avicel RC-591, FMC Corporation) and 120 g of sodium lauryl sulfate through a No. 30 mesh screen. The mixture was blended for ten minutes. To the mixture was added 250 g of magnesium stearate and 500 g of stearic acid powder through a No. 30 mesh screen. Mixing was continued for an additional five minutes after which the granulation was discharged into a clean polyethylene lined drum, yielding 49.20 kg of material.

This was then compressed on a Manisty Express Tabletting Machine using appropriate tooling.

The resulting tablets were coated in a 48 inch Accela Cota with an aqueous film coating mixture consisting of hydroxypropyl methylcellulose 7% w/w, polyethylene glycol 2% w/w, propylene glycol 3% w/w, and benzyl alcohol 1% w/w. The tablets were then placed on paper-lined trays to dry.

The tablelts prepared by the preceding method had the following per tablet unit formula:

| | weight (mg) | weight percent |
|---|---|---|
| fenoprofen calcium | 700.0 | 71.03 |
| lactose | 105.7 | 10.73 |
| starch powder | 70.0 | 7.10 |
| pregelatinized starch | 26.25 | 2.66 |
| povidone | 26.25 | 2.66 |
| opaspray butterscotch | 9.9 | 1.00 |
| cellulose with sodium CMC-591 | 30.0 | 3.04 |
| sodium lauryl sulfate | 2.4 | 0.24 |
| magnesium stearate | 5.0 | 0.51 |
| stearic acid powder | 10.0 | 1.01 |
| clear film coat (theory) | 19.32 | |

The tablet has the following dissolution rsults when evaluated according to the procedure described above.

| Time (minutes) | percent dissolved |
|---|---|
| 60 | 7 |
| 120 | 17 |
| 240 | 33 |
| 360 | 48 |
| 480 | 60 |

BIOAVAILAVILITY STUDY

The formulation of Example 1 was tested in a multiple dose study designed to compare the bioavailability of this formulation with Nalfon 600 mg tablets on successive days of psuedo-steady state treatment. The sustained release formulation of Example 1 was given as two 600 mg tablets every twelve hours, while the immediate release Nalfon 600 mg tablets were given as 1 tablet every six hours. This was a cross-over clinical study involving eighteen normal volunteers. Plasma samples were drawn on days five and six to determine blood levels of fenoprofen. The following abbreviations are used in the Table:

AUC—Area under the plasma concentration curve
Cpss—Mean Steady State plasma concentration (AUC O-T/T)
Cmax—Mean maximal plasma concentration
Cmin—Mean minimal plasma concentration
Cmax-Cmin—Mean plasma concentration
Tmax—Mean time to maximal concentration

| | Formulation | |
|---|---|---|
| | Nalfon IR | Example 1 |
| Total daily dose | 2400 mg | 2400 mg |
| Dosing Interval | 6 hours | 12 hours |
| Day 5 (96–102 hrs) | | |
| AUC(0–12)mcg*hr/ml | 338.8+/−84.4 | 356.7+/−85.4 |
| Cpss(mcg/ml) | 28.23 | 29.73 |
| Cmax(mcg/ml) | 57.7+/−14.4 | 57.6+/−14.0 |
| Cmin(mcg/ml) | 9.45+/−3.76 | 8.37+/−4.28 |
| Cmax-Cmin | 48.25 | 49.23 |

-continued

| | Formulation | |
|---|---|---|
| | Nalfon IR | Example 1 |
| Tmax(hrs.) | 0.94+/−0.73 | 2.1+/−1.1 |
| Day 6 (120-132 hrs) | | |
| AUC(0–12)mcg*hr/ml | 354.8+/−76.9 | 353.0+/−83.1 |
| Cpss(mcg/ml) | 29.57 | 29.41 |
| Cmax(mcg/ml) | 61.38+/−16.65 | 61.4+/−14.6 |
| Cmin(mcg/ml) | 11.66+/−5.35 | 9.16+/−5.56 |
| Cmax-Cmin | 49.72 | 52.24 |
| Tmax(hrs.) | 1.05−/−0.94 | 2.4+/−1.7 |

The following Examples illustrates the manufacture of a formulation of the invention with a Hobart mixer.

EXAMPLE 2

Mixture A was prepared as follows. A Hobart mixer was charged with 2.0 kg of fenoprofen calcim, 200 g of strearic acid power, 100 g of lactose, 200 g of starch powder, and 75 g of pregelatinized starch through an appropriate screen. This mixture was blended throughly and then granulated with 750 ml of a 10% w/v aqueous povidone solution. Purified water was added in a sufficient quantity to produce a satisfactory granulation. Total granulating time was between five and ten minutes. The wet granulation was placed through a No. 6 mesh screen onto paper-lined trays. The granulation was then dried in a dryhouse at 40° C. for 14 hours. The dried granulations were placed through a No. 16 mesh screen into an appropriate container.

A second mixture, hereinafter termed "mixture B", was prepared as follows. To a Hobart mixer was added 2.0 kg of fenoprofen calcium, 200 g of stearic acid powder, 100 g of lactose, 200 g of starch powder and 75 g of pregelatinized starch. This mixture was blended thoroughly and then granulated with 750 ml of a 10% w/v aqueous povidone solution containing 50 g of Opaspray Gold L-2106 (Colorcon, Inc). Purified water was added in a quantity sufficient to produce a satisfactory granulation. Total granulating time was between five and ten minutes. The wet granulation was placed through a No. 6 screen onto paper-lined trays. The granulation was dried in a dryhouse at 40° C. for 14 hours. The granulation was then placed through a No. 16 mesh screen into an appropriate container.

A V-blender was charged with 2.32 kg of mixture A and 2.36 kg of mixture B. To this mixture was added 125 g of lactose spray dried through a No. 30 mesh screen. This mixture was blended for ten minutes and 37.5 g of magnesium stearate was added through a No. 30 mesh screen. This was mixed for five minutes and then discharged into an appropriate container. The resulting mixture was compressed on a Stokes F-Press tabletting machine using appropriate tooling.

This particular formulation was not film coated prior to in vitro or in vivo evaluation.

| Per Tablet Unit Formula: | | |
|---|---|---|
| | Weight (mg) | Weight percent |
| fenoprofen calcium | 700.0 | 72.25 |
| stearic acid powder | 70.0 | 7.23 |
| lactose | 35.0 | 3.61 |
| starch powder | 70.0 | 7.23 |
| pregelatinized starch | 26.3 | 2.71 |
| povidone | 26.3 | 2.71 |
| Opaspray Gold | 8.7 | 0.90 |
| lactose spray dried | 25.0 | 2.58 |
| magnesium stearate | 7.5 | 0.77 |

The dissolution of these tablets was evaluated by the previously described method with the following results.

| |
|---|
| 60 min - 6% dissolved |
| 120 min - 10% dissolved |
| 240 min - 17% dissolved |
| 360 min - 23% dissolved |

BIOAVAILABILITY STUDY

This formulation was administered in a single-dose crossover study designed to compare the absorption profile and bioavailability with Nalfon 600 mg tablets (Immediate Release). Twelve male subjects between the ages of 22 and 46 were employed. The formulations were given after an overnight fast by the subjects. The subjects fasted for two hours before they received a standard breakfast meal.

The result of this study are presented below:

| Formulation | AUC(0-24) (hrs. mcg/ml) | % STD | Cmax (mcg/ml) | Tmax (hrs.) |
|---|---|---|---|---|
| Example 2 | 158.16+/−32.23 | 83.2% | 18.00+/−5.55 | 6.29+/−4.10 |
| Nalfon IR | 188.32+/−30.39 | 100% | 39.15+/−10.65 | 2.83+/−2.59 |

EXAMPLE 3

Mixture A was prepared as follows. A Hobart mixer was charged with 800 g of fenoprofen calcium, 80 g of stearic acid powder, 40 g of lactose, 80 g of starch powder and 30 g of pregelatinized starch through an appropriate screen. This mixture was blended thoroughly and then granulated with 300 ml of 10% w/v aqueous povidone solution. Purified water was added in a sufficient quantity to produce a satisfactory granulation. Total granulating time was between five and ten minutes. The wet granulation was placed through a No. 6 mesh screen onto paper-lined trays. The granulation was then dried at 40° C. for 14 hours. The dried granulation was placed through a No. 16 mesh screen into an appropriate container.

A second mixture, hereinafter termed "mixture B", was prepared as follows. To a Hobart mixer was added 2.4 kg of fenoprofen calcium, 240 g of stearic acid powder, 120 g of lactose, 240 g of starch powder and 90 g of pregelatinized starch through an appropriate screen. This mixture was blended thoroughly and then granulated with 900 ml of a 10% w/v aqueous povidone solution containing 45 g of Opaspray Butterscotch L-2701 (Colorcon, Inc.). Purified water was added in a quantity sufficient to produce a satisfactory granulation. Total granulating time was between five and ten minutes. The wet granulation was placed through a No. 6 screen onto paper-lined trays. The granulation was dried in a dryhouse at 40° C. for 14 hours. The granulation was then placed through a No. 16 screen into an appropriate container.

A V-blender was charged with 928 g of mixture A and 2822 g of mixture B. To this mixture was added 100 g of cellulose with sodium CMC-591 (Avicel RC 591) and 9.6 g of sodium lauryl sulfate through a No. 30 mesh screen. This mixture was blended for ten minutes after which 50 g of magnesium stearate was added through a No. 30 mesh screen. The mixture was mixed for five minutes and then discharged into an appropriate container. The resulting mixture was then compressed on a Stokes F-press tabletting machine using appropriate tooling.

These tablets were then film coated with an aqueous film coating mixture, consisting of hydroxypropyl methylcellulose 7% w/w, polyethylene glycol 2% w/w, propylene glycol 3% w/w, an benzyl alcohol 1% w/w in a conventional coating pan. The tablets were then placed onto paper-lined trays to dry.

| Per Tablet Unit Formula: | | |
|---|---|---|
| | Weight (mg) | Weight percent |
| fenoprofen calcium | 700.0 | 71.63 |
| stearic acid powder | 70.0 | 7.16 |
| lactose | 35.0 | 3.58 |
| starch powder | 70.0 | 7.16 |
| pregelatinized starch | 26.25 | 2.69 |
| povidone | 26.25 | 2.69 |
| Opaspray Butterscotch | 9.9 | 1.01 |
| cellulose with sodium CMC-591 | 25.0 | 2.56 |
| sodium lauryl sulfate | 2.4 | 0.25 |
| magnesium stearate | 12.5 | 1.28 |
| clear film coat (theory) | 25.5 | |

The dissolution of these tablets was tested by the previously described method to provide the following results.

| |
|---|
| 60 min - 6% |
| 120 min - 12% |
| 240 min - 25% |
| 360 min - 35% |
| 480 min - 47% |

Bioavailability Study

The formulation of Example 3 was administered in a single-dose crossover study designed to compare the absorption profile and bioavailability of the formulation with 2 X Nalfon 300 mg capsules (Immediate Release). Twelve male subjects between the ages of 22 and 46 were employed. The formulations were given after an overnight fast by the subjects. The subjects fasted for two hours before they received a standard breakfast meal.

The results of this study are presented below:

| Formulation | AUC(0-24) (hrs. mcg/ml) | % STD | Cmax (mcg/ml) | Tmax (hrs.) |
|---|---|---|---|---|
| Example 3 | 162.4+/−51.9 | 89.8% | 15.3+/−4.2 | 4.4+/−2.5 |
| Nalfon IR | 178.3+/−49.9 | 100% | 48.6+/−6.8 | 1.1+/−0.6 |

EXAMPLE 4

Mixture A was prepared as follows: A Hobart mixer was charged with 800 g of fenoprofen calcium, 120 g of lactose, 80 g of starch powder and 30 g of pregelatinized starch through an appropriate screen. This mixture was blended thoroughly and then granulated with 300 ml of 10% w/v aqueous povidone solution. Purified water was added in a sufficient quantity to produce a satisfactory granulation. Total granulating time was between five and ten minutes. The wet granulation was placed through a No. 6 mesh screen and onto paper-lined trays, and dried at 40° C. for 10 hours. The dried granulation was placed through a No. 16 mesh screen into an appropriate container.

A second mixture, hereinafter termed "mixture B", was prepared as follows. To a Hobart mixer was added 2.4 kg of fenoprofen calcium, 360 g of lactose, 240 g of starch powder and 90 g of pregelatinized starch through an appropriate screen. This mixture was blended thoroughly and then granulated with 900 ml of a 10% w/v aqueous povidone solution containing 45 g of Opaspray Butterscotch L-2701. Purified water was added in a quantity sufficient to produce a satisfactory granulation. Total granulating time was between five and ten minutes. The wet granulation was placed through a No. 6 screen onto paper-lined trays. The granulation was dried at 40° C. for 10 hours. The granulation was then placed through a No. 16 screen into an appropriate container.

A V-blender was charged with 928 g of mixture A and 2822 g of mixture B. To this mixture was added 100 g of lactose spray dried through a No. 30 mesh screen and 9.6 g of sodium lauryl sulfate. This mixture was blended for ten minutes after which 50 g of magnesium stearate was added through a No. 30 mesh screen. This mixture was mixed for five minutes and then discharged into an appropriate container. The resulting mixture was then compressed on a Stokes F-press tabletting machine using appropriate tooling.

These tablets were then film coated with an aqueous film coating mixture, consisting of hydroxypropyl methylcellulose 7% w/w, polyethylene glycol 2% w/w, propylene glycol 3% w/w, and benzyl alcohol 1% w/w in a conventional coating pan. The tablets were then placed onto paper-lined trays to dry.

| Per Tablet Unit Formula: | | |
|---|---|---|
| | Weight (mg) | Weight percent |
| fenoprofen calcium | 700.00 | 71.63 |
| lactose | 105.00 | 10.74 |
| starch powder | 70.00 | 7.16 |
| pregelatinized starch | 26.25 | 2.69 |
| povidone | 26.25 | 2.69 |
| Opaspray Butterscotch | 9.90 | 1.01 |
| lactose spray dried | 25.00 | 2.56 |
| sodium lauryl sulfate | 2.40 | 0.25 |
| magnesium stearate | 12.50 | 1.28 |
| clear film coat (theory) | 25.50 | |

The dissolution of these tablets was evaluated by the previously described method with the following results.

| |
|---|
| 60 min - 53% |
| 120 min - 76% |
| 240 min - 88% |

```
360 min - 91%
480 min - 94%
```

Bioavailability Study

The formulation of Example 4 was administered in a single-dose crossover study designed to compare the absorption profile and bioavailability of the formulation with 2 X Nalfon 300 mg capsules (Immediate Release). Twelve male subjects between the ages of 22 and 46 were employed. The formulations were given after an overnight fast by the subjects, and two hours before the subjects received a standard breakfast meal.

The results of this study are presented below:

| Formulation | AUC(0-24) (hrs. mcg/ml) | % STD | Cmax (mcg/ml) | Tmax (hrs.) |
|---|---|---|---|---|
| Example 4 | 159.3+/−57.1 | 87.8% | 16.0+/−4.7 | 3.1+/−2.1 |
| Nalfon IR | 178.3+/−49.9 | 100% | 48.6+/−6.8 | 1.1+/−0.6 |

EXAMPLE 5

A Diosna P-25 mixer was charged with 4.8 kg of fenoprofen calcium, 240 g of stearic acid powder, 480 g of lactose, 480 g of starch powder and 180 g of pregelatinized starch through a No. 10 mesh screen. This mixture was blended using the low speed mixer and low speed chopper settings for five minutes. While continuing to mix as described above, 1500 ml of a 12% w/v aqueous povidone solution was added slowly. The mixture was then agitated on the high speed chopper and high speed mixer settings for three minutes. During this time, purified water was added in quantity sufficient to make a satisfactory granulation. The granulation was then wet sieved through a No. 8 mesh screen onto paperlined trays. These were dried in a dryhouse at 110° F. for 18 hours. The dried granulation was then sieved through a No. 16 mesh screen by hand into an appropriate container.

A V-Blender was charged with 1391 g of this granulation. To this was added 112.5 g of cellulose with sodium CMC-591 and 3.6 g of sodium lauryl sulfate through a No. 30 mesh screen. This mixture was blended for ten to fifteen minutes after which 18.75 g of magnesium stearate was added through a No. 30 mesh screen. This was mixed for five minutes and then discharged into an appropriate container. The resulting mixture was compressed on a Stokes F-press tabletting machine using appropriate tooling.

| Per Tablet Unit Formula: | Weight (mg) | Weight percent |
|---|---|---|
| fenoprofen calcium | 700.00 | 68.80 |
| stearic acid powder | 35.00 | 3.44 |
| lactose | 70.00 | 6.88 |
| starch powder | 70.00 | 6.88 |
| pregelatinized starch | 26.25 | 2.58 |
| povidone | 26.25 | 2.58 |
| cellulose with sodium CMC-591 | 75.00 | 7.37 |
| sodium lauryl sulfate | 2.40 | 0.24 |
| magnesium stearate | 12.50 | 1.23 |

We claim:

1. A sustained release pharmaceutical formulation in tablet unit dosage form which provides prolonged plasma levels of an active agent and comprises about 60.0% to about 80.0% by weight of the active agent, about 1.0% to about 15.0% by weight of a pharmaceutically acceptable excipient, about 3.0% to about 15.0% by weight of a disintegrant, about 2.0% to about 10.0% by weight of a pharmaceutically acceptable binder and about 0.5% to about 3.0% by weight of a tablet lubricant.

2. A formulation of claim 1 wherein the active agent is fenoprofen calcium.

3. A formulation of claim 2 which contains from about 0.1% to about 2.0% by weight of a surface active agent.

4. A formulation of claim 1 wherein the active agent is selected from the group consisting of fenoprofen, aspirin, sodium salicylate, phenyl butazone, oxyphenbutazone, apazone, indomethacin, sulindac, mefenamic acid, meclofenamic acid, flufenamic acid, tolfenamic acid, etofenamic acid, tolmetin sodium, ibuprofen, naproxen, flurbiprofen and ketoprofen.

* * * * *

REEXAMINATION CERTIFICATE (1747th)
United States Patent [19]
Oren et al.

[11] B1 4,753,801
[45] Certificate Issued Jul. 14, 1992

[54] SUSTAINED RELEASE TABLETS

[75] Inventors: Peter L. Oren, Noblesville; Werner M. K. Seidler, Indianapolis, both of Ind.

[73] Assignee: Eli Lilly and Company, Indianapolis, Ind.

Reexamination Request:
No. 90/002,303, Mar. 22, 1991

Reexamination Certificate for:
Patent No.: 4,753,801
Issued: Jun. 28, 1988
Appl. No.: 791,282
Filed: Oct. 25, 1985

[51] Int. Cl.⁵ .................... A61K 9/22; A61K 9/26

[52] U.S. Cl. .................... 424/465; 424/469;
514/165; 514/243; 514/404; 514/420; 514/423;
514/567; 514/569; 514/570

[58] Field of Search .................... 424/464, 465, 468

[56] References Cited

U.S. PATENT DOCUMENTS

| | | | |
|---|---|---|---|
| 4,264,573 | 4/1981 | Powell et al. | 424/19 |
| 4,308,251 | 12/1981 | Dunn et al. | 424/19 |
| 4,309,404 | 1/1982 | DeNeale et al. | 424/21 |
| 4,369,172 | 1/1983 | Schor et al. | 424/19 |
| 4,601,894 | 7/1986 | Hanna et al. | 424/19 |

*Primary Examiner*—Thurman K. Page

[57] ABSTRACT

The present invention provides sustained release tablets in unit dosage form comprising an active agent which has low aqueous solubility.

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-4 are cancelled.

* * * * *